(12) United States Patent
Tas

(10) Patent No.: US 6,929,692 B2
(45) Date of Patent: Aug. 16, 2005

(54) CALCIUM PHOSPHATE CEMENT COMPOSITION AND A METHOD FOR THE PREPARATION THEREOF

(75) Inventor: Ahmet Cüneyt Tas, Central, SC (US)

(73) Assignee: Biomet Deutschland GmbH, Berlin (DE)

( * ) Notice: Subject to any disclaimer, the term of this patent is extended or adjusted under 35 U.S.C. 154(b) by 77 days.

(21) Appl. No.: 10/647,438

(22) Filed: Aug. 26, 2003

(65) Prior Publication Data

US 2004/0112256 A1 Jun. 17, 2004

(30) Foreign Application Priority Data

Aug. 27, 2002 (EP) .............................................. 02019214

(51) Int. Cl.[7] .............................................. C04B 12/02
(52) U.S. Cl. ........................................ 106/690; 106/35
(58) Field of Search .................................. 106/35, 690

(56) References Cited

U.S. PATENT DOCUMENTS 5,605,713 A * 2/1997 Boltong ...................... 427/2.1

6,616,742 B2 * 9/2003 Lin et al. ...................... 106/35

OTHER PUBLICATIONS

Huipin Yuan et al., "Tissue responses of calcium phosphate cement: a study in dogs", ELSEVIER Biomaterials 21 (2000) pp. 1283–1290.

* cited by examiner

Primary Examiner—J. A. Lorengo
Assistant Examiner—Shalie A. Manlove
(74) Attorney, Agent, or Firm—Millen White Zelano & Branigan P.C.

(57) ABSTRACT

The invention describes a new calcium phosphate cement powder, whose composition can best be described over the Ca/P molar ratio range of 1.35 to 1.40, most preferably 1.39, and whose two components were prepared by wet chemical synthesis procedures. One component is chemically-synthesized, bi-phasic alpha-TCP ($Ca_3(PO_4)_2$, 95 wt %)+HA ($Ca_{10}(PO_4)_6(OH)_2$, 5 wt %) powder, while the second component is again a chemically-synthesized, single-phase DCPD ($CaHPO_4 \cdot 2H_2O$) powder. A setting solution ($Na_2HPO_4 \cdot 2H_2O$) is used to form a self-setting calcium phosphate cement from the powder mixture. This cement can be used as bone filler or bone substitute in applications, which require higher rates of resorption.

20 Claims, 8 Drawing Sheets

CALCIUM PHOSPHATE CEMENT COMPOSITION AND A METHOD FOR THE PREPARATION THEREOF

The invention describes a new calcium phosphate cement powder, whose composition can best be described over the Ca/P molar ratio range of 1.35 to 1.40, optimally 1.39, and whose two components were prepared by wet chemical synthesis procedures. One component is chemically-synthesized, bi-phasic alpha-TCP ($Ca_3(PO_4)_2$, 95 wt %)+HA ($Ca_{10}(PO_4)_6(OH)_2$, 5 wt %) powder, while the second component is again a chemically-synthesized, single-phase DCPD ($CaHPO_4 \cdot 2H_2O$) powder. A setting solution (3 wt % $Na_2HPO_4 \cdot 2H_2O$ dissolved in distilled water) is used to form a self-setting calcium phosphate cement from the powder mixture. This cement can be used as bone filler or bone substitute in applications, which require higher rates of resorption.

BACKGROUND OF THE INVENTION

Calcium phosphate-based cements (a.) H. Monma and T. Kanazawa, "Wet-Process Formation of Non-stoichiometric Hydroxyapatite from Tricalcium Phosphate," Yogyo Kyokaishi, 86, 73–76, 1978, b.) W. E. Brown and L. C. Chow, "A New Calcium Phosphate Water Setting Cement"; pp. 352–77 in Cements Research Progress-1986, Edited by P. W. Brown. American Ceramic Society, Westerville, Ohio, 1987, c.) A. A: Mirtchi, J. Lemaitre, and E. Munting, "Calcium Phosphate Cements: Study of the beta-tricalcium Phosphate-Dicalcium Phosphate-Calcite Cements," Biomaterials, 11, 83–88, 1990, d.) F. C. M. Driessens, J. A. Planell, et al., Bioceramics, 10, 279–82, 1997, e.) K. S. TenHuisen and P. W. Brown, "Formation of Calcium-Deficient Hydroxyapatite from alpha-$Ca_3(PO_4)_2$," Biomaterials, 19, 2209–17, 1998.) are conventionally prepared by mixing calcium phosphate powders of a special composition and a kneading liquid, such as distilled water, for example, in a mortar to obtain kneaded cement which may then be filled into or applied to a defective portion of bone (or tooth) using a syringe or spatula or hand and then allowed to cure.

Calcium phosphate-based cements are usually desired to be almost identical with the chemical composition of the inorganic component of bones or teeth, which is carbonated, deficient or stoichiometric "calcium hydroxyapatite." However, in recent years with an increase in the number of animal studies performed with such materials, it is becoming more and more evident that the calcium hydroxyapatite bioceramic, when prepared synthetically or even when taken from bovine sources in highly porous forms (i.e., granules or blocks), has very low bioresorbability (M. T. Mushipe, P. A. Revell, and J. C. Shelton, "Cancellous Bone Repair using Bovine Trabecular Bone Matrix Particulates," Biomaterials, 23, 365–370, 2002), and moreover, if it is stoichiometric (i.e., its Ca/P molar ratio being equal to 1.67) it almost doesn't take part in the bone remodelling processes which were initiated and performed by the bone cells in vivo.

Calcium phosphate-based cements when they are prepared by using calcium phosphate powder formulations which have a Ca/P molar ratio values higher than 1.50 (e.g., F. C. M. Driessens, M. G. Boltong, E. A. P. De Maeyer, R. M. H. Verbeeck, and R. Wenz, "Effect of temperature and immersion on the setting of some calcium phosphate cements," J. Mater. Sci. Mater. Medic., 11, 453–57, 2000) do also show reduced levels of resorbability (as compared to calcium phosphate cements (e.g., U.S. Pat. No. 6,117,456) of lower Ca/P molar ratios) when implanted in vivo.

However, the Ca/P molar ratio of calcium phosphate-based cements do not alone dictate the extent of in vivo resorbability of these. Together with the appropriate adjustment of the overall Ca/P ratio, the proper choice of the calcium phosphate compounds (in an order of decreasing in vitro solubility at neutral pH values: TTCP ($Ca_4(PO_4)_2O$), alpha-TCP ($Ca_3(PO_4)_2$), MCPM ($Ca(H_2PO_4)_2 \cdot H_2O$), beta-TCP, $Ca_2P_2O_7$, DCPD ($CaHPO_4 \cdot 2H_2O$), DCPA ($CaHPO_4$), or HA ($Ca_{10}(PO_4)_6(OH)_2$)) to be used in the design of cements becomes the crucial factor in tailoring the resorbability of a new cement.

In selecting the calcium phosphate compounds (either from the binary system of CaO—$P_2O_5$ or from the ternary system of CaO—$P_2O_5$—$H_2O$) to form a cement powder out of those, utmost care and priority must also be given to the in vitro/in vivo solubility (and the rate of hydrolysis of those in media similar to human plasma) of the candidates under consideration.

Calcium phosphate cements for living bodies have an advantage that most of them transform into a bioactive hydroxyapatite (also known as "apatitic tricalcium phosphate," $Ca_9(HPO_4)(PO_4)_5OH$) upon hardening, and hence result in a hardened cement having excellent bioaffinity. Many of the already known calcium phosphate cements for living bodies comprise tetracalcium phosphate (TTCP, $Ca_4(PO_4)_2O$) as the main component. For example, U.S. Pat. No. 4,612,053 and EP No. 1172076 disclose cements comprising tetracalcium phosphate and dicalcium phosphate anhydrous (DCPA, $CaHPO_4$) as the main components, whereas the U.S. Pat. No. 5,525,148 describes the preparation of a series of calcium phosphate cements which do not contain any TTCP. It is also known that the hardening properties (i.e., setting times (typically measured in the dry state) and final compressive strengths achieved following immersion in pseudo or real physiological fluids) of these calcium phosphate cements widely vary also depending on the amount of liquid employed in the step of kneading. That is, the hardening time is shortened while the strength of the hardened body is elevated with a decrease in the kneading liquid employed.

The most popular TTCP-containing cement (whose secondary component being the acidic calcium phosphate, MCPM: $Ca(H_2PO_4)_2 \cdot H_2O$) is known under the commercial name of "Norian SRS," and it has a compressive strength in the vicinity of 40 MPa, according to its manufacturer (Norian Corporation). This cement has a Ca/P molar ratio slightly greater than 1.50. Its in vivo resorbability still requires the disclosure of animal and clinical tests from independent sources.

U.S. Pat. No. 6,117,456 discloses the preparation of a highly resorbable (complete in vivo resorption in less than a year) cement of the name alpha-BSM (which is marketed in Europe (by Biomet-Merck) under the name of "BIOBON®"). This cement consists of two powder components, (i) poorly crystalline calcium phosphate (major phase), and (ii) well-crystallized DCPD (Brushite, $CaHPO_4 \cdot 2H_2O$). BIOBON® has a Ca/P molar ratio less than 1.50. Although it is major, poorly crystalline calcium phosphate component reacts quite rapidly (started within the first 24 hours, and continues with the passage of time) to form apatitic tricalcium phosphate ($Ca_9(HPO_4)(PO_4)_5OH$), the full resorption of the crystalline component takes significantly longer to take place. BIOBON® (or alpha-BSM), which is kneaded with a simple saline solution to form its paste, suffers from extremely low compressive strength values (in the vicinity of 10 to 15 MPa) upon full setting, and this severely limits its usage mainly to "non-load-bearing" places and applications.

U.S. Pat. No. 5,152,836 describes a calcium phosphate cement (again with a Ca/P molar ratio slightly greater than 1.50) composed of alpha-TCP (75 wt %), TTCP (18 wt %), DCPD (5 wt %), HA (2 wt %), kneaded into a paste with a relatively concentrated aqueous solution of chondroitin sulphate and sodium succinate. This cement has been in the market under the commercial name of BIOPEX®) (Mitsubishi Material Co.). It is claimed to achieve a compressive strength of 60 to 90 MPa. Little is known about its resorbability, but it is claimed by its manufacturer to resorb quite fast (around 50% in few weeks).

The newest calcium phosphate cement commercially available on the market is known as CALCIBON® (produced and marketed by Biomet-Merck) with a Ca/P molar ratio of 1.55, and it consists of a mixture of alpha-TCP (58–60 wt %), DCPA.(26–27 wt %), $CaCO_3$ (12–13 wt %), and HA (2%). It has a compressive strength over the range of 50–60 MPa, and in the bulk form (i.e., without any significant macroporosity) it is not as fast-resorbable as BIOBON®. High compressive strength calcium phosphate cements are nevertheless still suitable for the repair of bone cavities or defects in load-bearing places of the living bodies.

Alpha-TCP, alone, is known to easily hydrolyze in vitro or in vivo directly into calcium-deficient hydroxyapatite (K. S. TenHuisen and P. W. Brown, "Formation of Calcium-Deficient Hydroxyapatite from alpha-$Ca_3(PO_4)_2$," Biomaterials, 19, 2209–17, 1998), and the Ca/P molar ratios in a wide family of "calcium-deficient hyroxyapatites" can take values over the range of 1.3 to 1.65. When these values are in excess of 1.50, and when they become progressively closer to that of stoichiometric hydroxyapatite (1.67), the resorbability of the implants is observed to decrease. On the other hand, if the formed calcium-deficient hydroxyapatites (as a result of the setting reaction) also contain alkali elements like Na and K, then the resorbability of the cements would also increase (F. C. M. Driessens, M. G. Boltong, E. A. P. de Maeyer, R. Wenz, B. Nies, and J. A. Planell, "The Ca/P Range of Nanoapatitic Calcium Phosphate Cements," Biomaterials, 23, 4011–17, 2002). The intentional doping of crystallographic Ca-sites in the newly forming calcium-deficient hydroxyapatite microstructure (which is typically imaged in electron microscope micrographs with microflakes or microneedles forming on the alpha-TCP grains) with such alkali elements leads to the generation of vacancies, and carbonate ion ($CO_3^{2-}$) substitutions in the hydroxyl sites and the phosphate ion sites, respectively. It also needs to be remembered hereby that the human bones contain around 1.6 wt % Na and K ions.

The primary powder components (i.e., alpha-TCP and TTCP) for almost all of the commercially available calcium phosphate cements, with the only exception of BIOBON®, have been prepared by solid-state reactive firing (SSRF) at high temperatures (in excess of 1350° C.). The use of such high temperatures during production inescapably lead to hard, sintered products with grain sizes mostly in excess of 80 to 100 $\mu$m, and therefore those components are needed to be grinded with high-energy mills, first, into a fine powder before their use in the cement formulations. High energy milling is generally performed for at least one hour in industrial rotating mills having hard (scratch-resistant) inner linings and hard balls, which can be made from agate or ceria-stabilized zirconia. Typically, the balls fill 20–25% of the volume of the mill and impact the material as the mill turns. These mills can increase the surface temperature of the individual particles and even cause undesirable mechanochemical reactions.

Fine powders (less than 30 $\mu$m) are strictly required in the calcium phosphate cement formulations in order to achieve higher rates of in vivo bioreactivity and biointegration with the ingrowing bone into the repair site. SSRF practices and the follow-up grinding operations naturally increase the costs of manufacturing of such cements.

SUMMARY OF THE INVENTION

A feature of the present invention is to provide a new calcium phosphate cement, which avoids the above-mentioned disadvantages from the prior art and having a Ca/P molar ratio significantly lower than 1.50, and whose major component being $\alpha$-$Ca_3(PO_4)_2$ (i.e., $\alpha$-TCP), a minor component being the high aqueous solubility calcium phosphate compound Brushite (DCPD: $CaHPO_4 \times 2H_2O$), and to contain a small amount of hydroxyapatite to serve as a seed to accelerate the formation of calcium-deficient hydroxyapatite.

Another feature of the invention is to provide a method of preparing an $\alpha$-TCP-based calcium phosphate cement, whose entire constituents are produced by wet-chemical synthesis routes, which at the same time facilitate easier alkali element (Na and K) doping into the cement body, and thereby eliminating the cost-increasing processing steps, such as the use of temperatures in excess of 1200° C. on the production floor, and tedious high-energy grinding operations for decreasing the particle sizes.

Upon further study of the specification and appended claims, further features and advantages of this invention will become apparent to those skilled in the art.

These and other features can be achieved by a method of preparing a calcium phosphate cement composition, characterized in that the method comprises the steps of:

a) adding a preheated $Ca(NO_3)_2 \times 4H_2O$ solution to a $(NH_4)_2HPO_4$ solution under stirring followed by addition of concentrated $NH_4OH$ solution and subsequently calcining at about 1180 to less than 1280° C., optimally about 1200° C., of 95wt % $\beta$-type calcium tertiary phosphate and 5 wt % hydroxyapatite to form biphasic powder A consisting of 95wt % $\alpha$-type calcium tertiary phosphate and 5 wt % hydroxyapatite.

b) adding a $Na_2HPO_4 \times 2H_2O$ solution to a $KH_2PO_4$ solution under stirring followed by adding of $Ca(NO_3)_2 \times 4H_2O$ to form single-phase powder B ($CaHPO_4 \times 2H_2O$).

c) mixing of powder A with powder B and subsequently lightly milling or grinding to form the cement powder with an overall molar ratio of Ca/P of 1.35 to 1.40, preferably 1.36–1.39, and optimally 1.39.

The calcium phosphate cement powder of this invention is formed by physically dry mixing two powders together. These powders are (a) Powder A: a bi-phasic mixture of alpha-TCP ($\alpha$-$Ca_3(PO_4)_2$)+HA ($Ca_{10}(PO_4)_6(OH)_2$), preferably 94:6–96:4, optimally 95:5 weight ratio of alpha-TCP:HA and (b) Powder B: DCPD ($CaHPO_4 \cdot 2H_2O$). Generally, when HA is less than 4%, cement setting time can increase significantly to around 30 minutes and is higher than 6%, the compressive strength of the formed cement can decrease to less than 10 MPa.

Afterwards, the dry mixture of A and B can be combined with a setting solution ($Na_2HPO_4 \times 2H_2O$) by an end user, e.g. a surgeon in an operating room.

These powders are prepared by wet-chemical synthesis procedures, whose details are given in the working examples below. Cement powder is obtained by blending generally at room temperature (e.g. 18–26° C.) 70 to 80 wt % powder A and 20 to 30 wt % powder B in a mill with one another. Preferred is a mixing ratio of 75:25 by weight. Generally, the adding b) and the mixing c) occurs at room temperature and atmospheric temperature.

The preferred setting solution to cause the initiation of the setting reaction, is an aqueous 3 wt % $Na_2HPO_4 \cdot 2H_2O$ solution. It is also observed that increasing the concentration of this solution to 4 wt % decreased the hardening time, while decreasing it (to 2 wt %) extended the hardening time beyond 30 minutes.

The preferred "liquid-to-powder" (i.e., UP) ratio for this cement is in the range of 0.40 to 0.45 mL of solution per gram of cement powder. The most preferred value is 0.43 mL.

When the Ca/P molar ratio is adjusted (by changing the mixing ratios of Powder A and Powder B) between 1.33 and 1.43, it is also observed that the setting reaction takes place. Starting from the lower end (1.33) of this Ca/P ratio range, in going to its upper end (1.43), compressive strength has the tendency to increase (from 34 to 39 MPa).

Calcined powders are lightly ground, as oppose to high energy milling, to obtain a fine powder with particles less than 40 µm. Light milling as practiced by the present invention can be accomplished in no more than 15 minutes. Moreover, the mill can have soft walls, such as polyethylene, and contain only a single ball. As an example, the milling can take place in a polyethylene bottle containing a ball by manually turning the bottle. Such light milling avoids the problems associated with high energy milling, such as mechanochemical reactions.

The setting solution may also be prepared by dissolving any one or more of the following chemicals in deionized water to achieve a 2 to 4 wt % solution: $Na_2HPO_4$, $NaH_2PO_4$, $K_2HPO_4$, $KH_2PO_4$, and, NaCl.

EXAMPLES

The invention is described in detail below in terms of the following working examples.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Example 1

Figure 4:
FIG. 4 is a SEM picture of a powder A at a scale of 30 µm.

Synthesis of Bi-phasic Alpha-TCP+HA Powders (Powder A):

51.53 g of $(NH_4)_2HPO_4$ is dissolved in a glass beaker in 650 mL distilled $H_2O$, preheated to 37° C., to form a clear solution (Solution A). In a separate glass beaker 139.35 g of $Ca(NO_3)_2·4H_2O$ is dissolved in 1000 mL of $H_2O$, preheated to 37° C., to form solution B. Solution B is slowly (in 5 minutes) added into solution A under constant stirring. The temperature of the opaque solution is maintained at 37° C. The nominal Ca/P molar ratio in this solution is 1.512. A 33 mL aliquot of concentrated (i.e., 25 vol %) $NH_4OH$ is then added at once to the milky solution, and stirred for 2 hours at 37° C. Formed precipitates are then filtered out of the mother liquor, washed with 2 liters of distilled water, and followed by drying in an air atmosphere at 60° C. for 24 hours. The dried powders are later calcined in an inert $Al_2O_3$ bowl at 850° C for 12 hours in an air atmosphere. Formed powders are found to consist of 95wt % beta-TCP and 5 wt % HA. These sub-micron particulated powders are then converted to 95wt % alpha-TCP+5 wt % HA by calcining at 1200° C. followed by quenching to room temperature. Calcination is performed as follows: 95wt % beta-TCP+5 wt % HA powders are heated (in an $Al_2O_3$ bowl) from room temperature to 1200° C. in 4 hours, soaked at 1200° C. for 3.5 hours, followed by quenching (in the furnace) from 1200° C. to 1000° C in 10 minutes, subsequent cooling from 1000°to 500° C. in 1 h, and final cooling to RT from 500° C. being achieved in 3 hours. Calcined powders are lightly ground to obtain a fine powder with particles less than 40 µm. (see FIG. 1 and FIG. 4)

Figure 1:
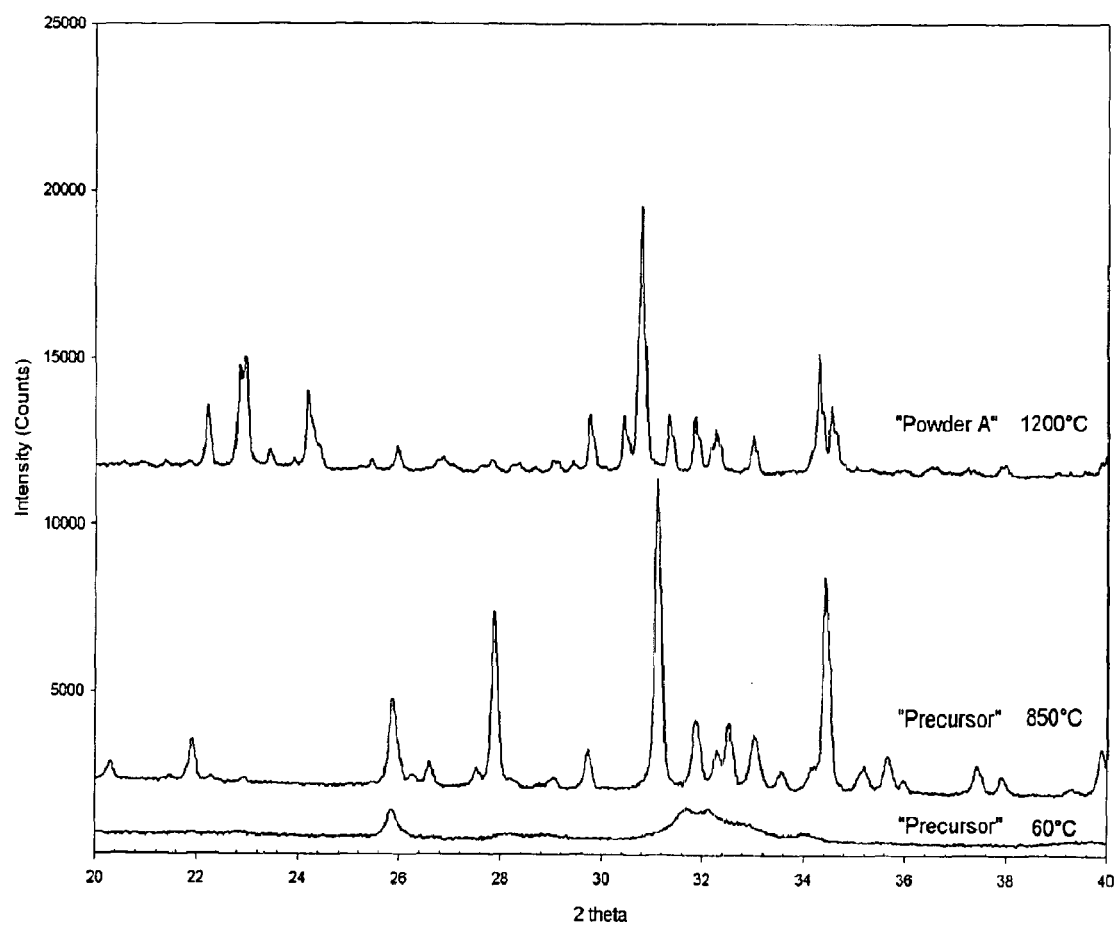
FIG. 1 depicts powder XRD traces of the precursors and the powder obtained in Example-1.

FIG. 1 shows the powder X-ray diffraction (XRD) data for the two precursors of powder A (obtained at 60° and 850° C.), and the data for the Powder A itself (after 1200° C. calcination) in one diagram.

Example 2

Synthesis of Brushite (DCPD: $CaHPO_4·2H_2O$) Powders (Powder B):

2.0636 g of $KH_2PO_4$ are dissolved in a glass beaker containing 1750 mL of distilled water at room temperature to prepare a clear solution. 7.5324 g of $Na_2HPO_4·2H_2O$ is then added into this solution and mixed for 15 minutes. The pH value of the resultant solution is measured to be 7.4. 27.59 g of $Ca(NO_3)_2·4H_2O$ (in powder form) is then added at once into the solution B, and mixed at room temperature for 80 minutes. Formed precipitates are then filtered out of the mother solution, washed with 2 liters of distilled $H_2O$, and dried at 60° C. for 24 hours. High crystallinity, single-phase DCPD ($CaHPO_4·2H_2O$) powders are obtained. Chemical analyses performed on these samples indicate the presence of 1.6 wt % Na and K, combined.

Figure 2:
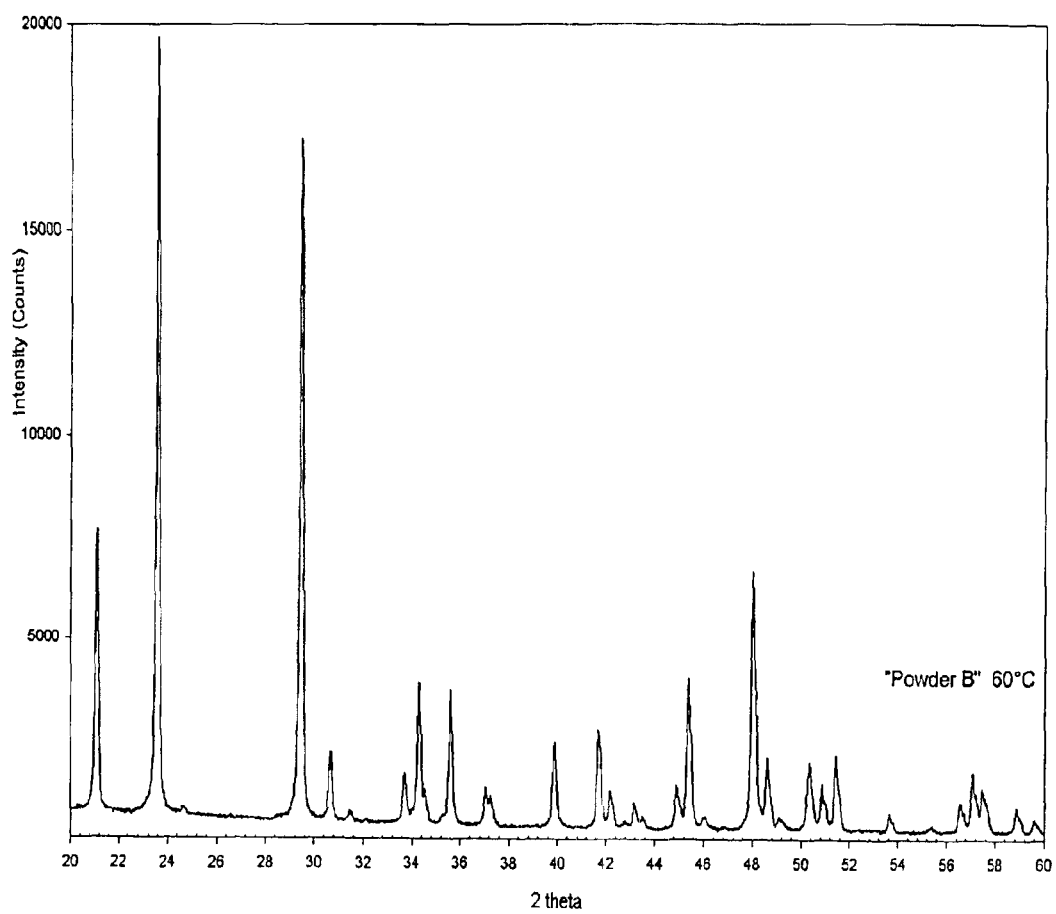
FIG. 2 depicts XRD data of the synthesized DCPD powders (Powder B).
Figure 5:
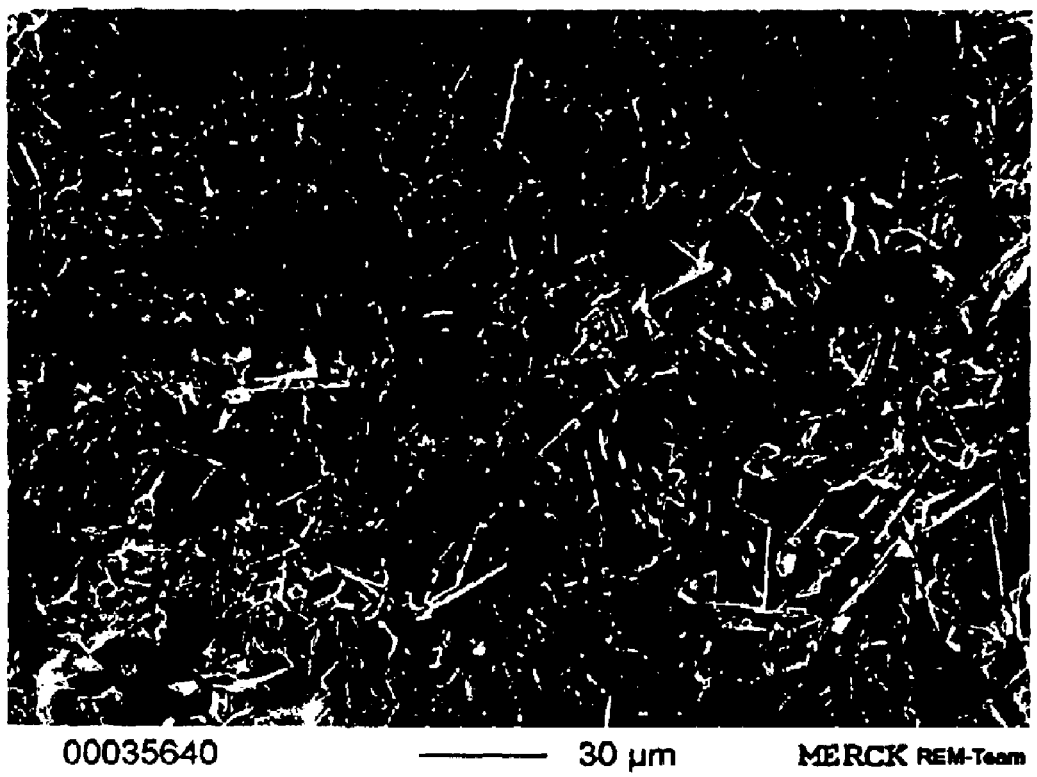
FIG. 5 is a SEM picture of a powder B at a scale of 30 µm.

FIG. 2 shows the XRD data of the DCPD powders of extremely high crystallinity. These powders have a plate-like morphology (visible by SEM pictures, see, e.g., FIG. 5).

Example 3

Figure 6:
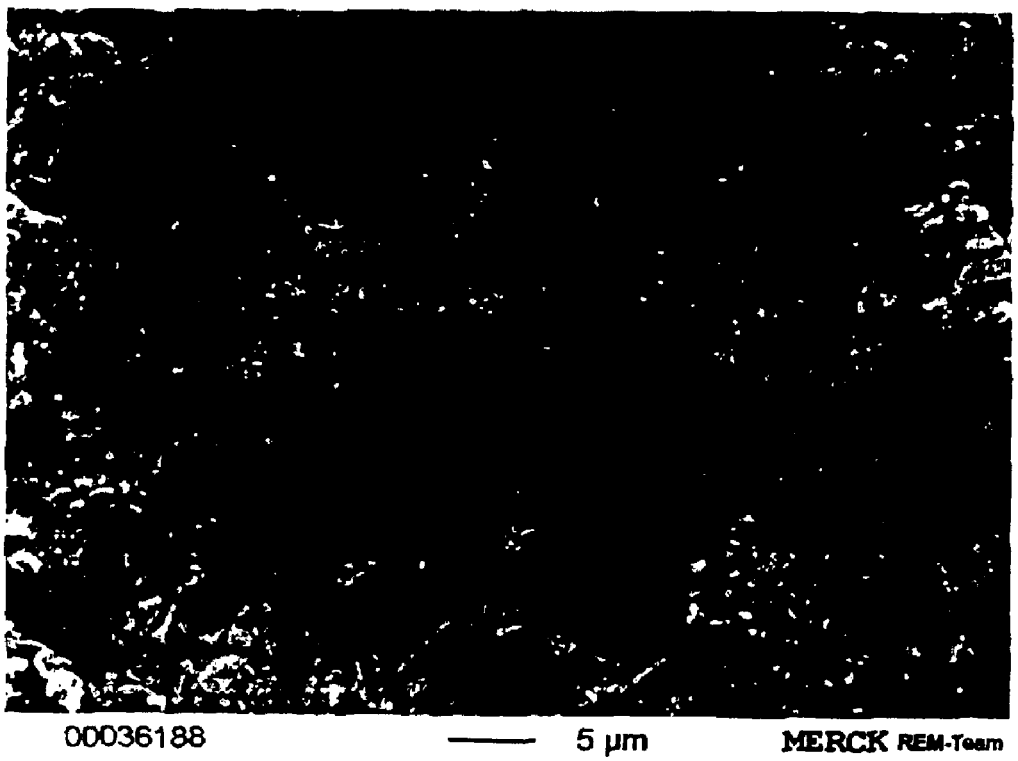
FIG. 6 is a SEM picture of a dry mixture of powders A and B at a scale of 5 µm.

Preparation of the Cement Powders:

Powder A (75 wt %) and Powder B (25 wt %) are placed in a plastic bottle (no grinding balls in it), tightly sealed, and then placed in an automatic mill (Turbula-type) for 1 hour. The total amount of the powder in the bottle is 100 grams. Cement powder is ready after this milling. By mixing these two powders, the phase assemblage of the cement powder corresponds to 71.1 wt % alpha-TCP, 25.2 wt % DCPD, and 3.7 wt % HA, with the overall Ca/P molar ratio being equal to 1.39. FIG. 6 is an SEM picture depicting a dry cement powder after mixing Powders A and B.

Example 4

Setting of the Cement:

The preferred setting accelerator solution is 3 wt % $Na_2HPO_4·2H_2O$ solution in distilled water. This solution is proven to perform well in alpha-TCP-based cements.

3.00 g Cement powder is first placed into an agate mortar. 1.30 mL of the setting solution is dropped onto the powder body, and the mixture is kneaded with an agate pestle for 90 seconds until the paste is formed. Hardening is observed in 10 to 12 minutes, meaning that before the reaching of the 10 minutes limit, the paste can be given any shape. The compressive strength is measured as 37±2 MPa.

The strength of this cement can be increased up to 50±3 MPa after 15 wt % beta-TCP whisker addition (synthesized in accordance with the procedure outlined in the reference: A. C. Tas, "Molten salt synthesis of calcium hydroxyapatite whiskers, " J. Am. Ceram. Soc., 84, 295–300, 2001) However, such additions do alter the overall Ca/P molar ratio of the original cement formulation.

Compressive strength values are measured in an Instron-tester after squeezing the pastes into 7.5 mm diameter, 1.4 cm tall cylindrical molds, followed by 72 hours of curing at 37° C. in deionized water, and drying.

Example 5
In Vitro Performance Evaluation of the Cement:

3.0 g of the cement powder is kneaded in an agate mortar with 1.3 mL of 3 wt % $Na_2HPO_4 \cdot 2H_2O$ solution for 90 seconds. Formed paste is given the shape of a 1 cm-diameter ball by hand. The samples are then placed in 30 mL of deionized water in sealed glass bottles and placed in an oven at 37° C. for periods ranging from 1 day to 3 months.

Figure 7:
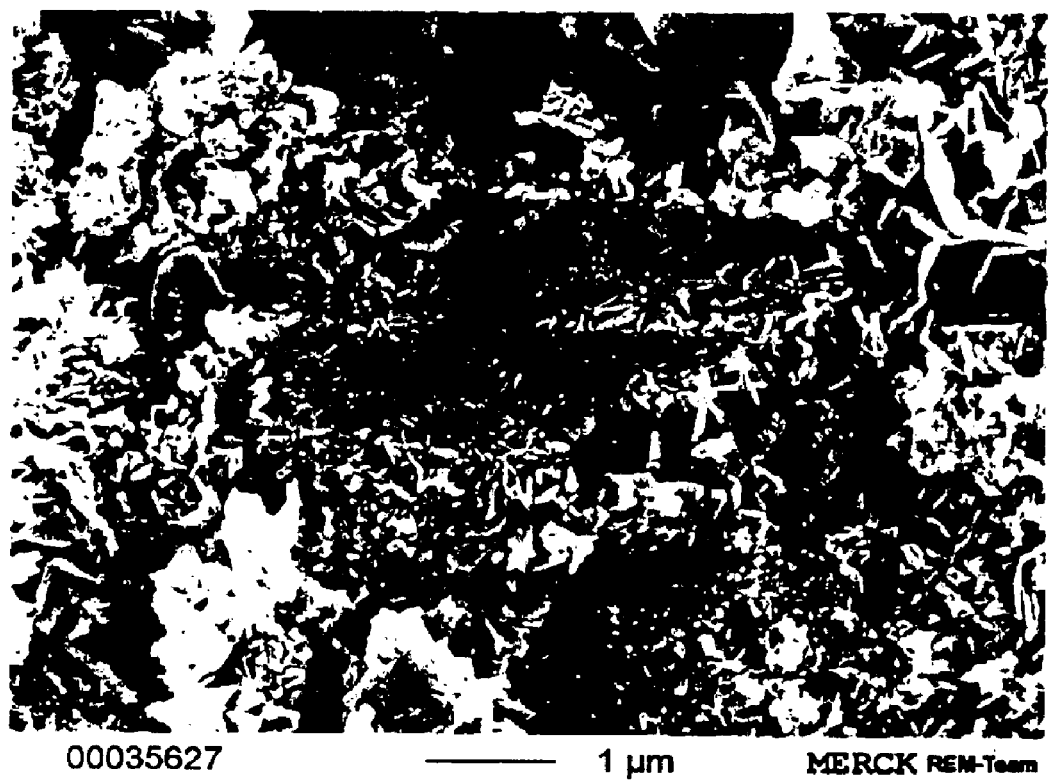
FIG. 7 is a SEM picture of a cement sample after kneading with a setting solution at a scale of 1 µm.

Scanning electron microscope (SEM) pictures show that the large plates of DCPD already started to transform into calcium-deficient hyroxyapatite (CDHA), whose characteristic morphology is those microflakes or needles. The major component of this cement, which is alpha-TCP (95%)+HA (5%), has also started to transform into CDHA, as evidenced by those microflakes. See FIG. 7 depicting a fracture surface of a cement sample after kneading with setting solution and storing in deionized water at 37° C. for 3 days. As depicted, the larger DCPD (originating from Powder B) plates turn into calcium-deficient hydroxyapatite (CDHA) microflakes.

Figure 8:
FIG. 8 is a SEM picture of a cement sample kept in deionized water at 37° C. for 3 months at a scale of 1 µm.

SEM pictures which show the morphology of the cement bulk after 3 months in $H_2O$ at 37° C. are characterized by an almost complete dissolution of the plates, leaving a porous cement body, which can be most suitable for the bone ingrowth to take place and proceed through. See FIG. 8 depicting a fracture surface of a cement sample after kneading with setting solution and storing in deionized water at 37° C. for 3 months. As depicted, almost all of the large DCPD plates have completed their transformation into CDHA, and the cement is advantageously porous.

Figure 3:
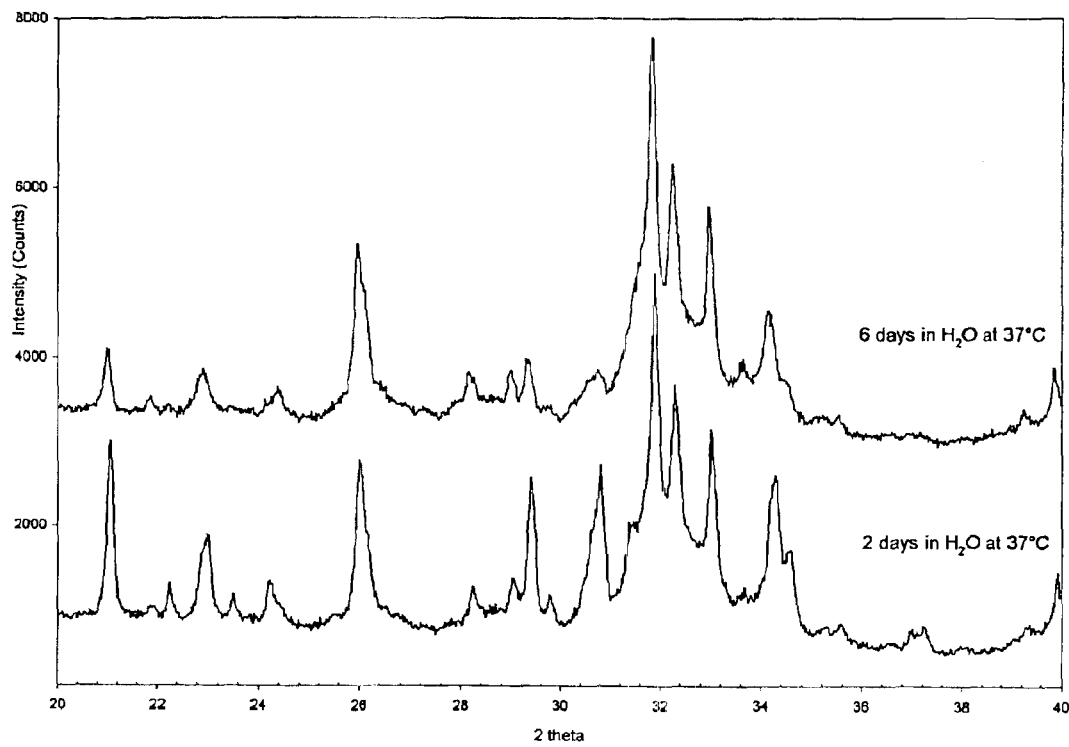
FIG. 3 depicts XRD data of cement samples soaked in water for few days.

Phase analyses of the cement samples soaked in water at 37° C. are reported by the powder XRD data given in FIG. 3. It is apparent from this data that CDHA peaks (at the 2 theta regions of around 26° and 31.9° and 35°) start to be visible even after two days of soaking, while the characteristic DCPD peaks (at around 21°, 23°, and 29.5°) are losing their intensity in going from 2 days to 6 days, meaning that they are rapidly dissolving, and turning the whole cement body eventually into one of calcium-deficient hydroxyapatite. CDHA is regarded as the only calcium phosphate compound which strongly resembles to the bone mineral.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosure of all applications, patents and publications, cited herein and of corresponding EP application No. 02019214.2, filed Aug. 27, 2002, is incorporated by reference herein.

What is claimed is:

1. A calcium phosphate cement composition, comprising:
   a biphasic powder A comprising $\alpha$-$Ca_3(PO_4)_2$ and $Ca_{10}(PO_4)_6(OH)_2$; and
   a single phase powder B comprising $CaHPO_4 \cdot 2H_2O$ wherein the cement has a molar ratio of Ca/P of 1.35–1.40.

2. A calcium phosphate cement composition of claim 1, wherein the powder A and the powder B are mixed in a mixing ratio of 70:30 to 80:20 by weight.

3. A calcium phosphate cement composition of claim 1, wherein the powder A and the powder B are mixed in a mixing ratio of 75:25 by weight.

4. A calcium phosphate cement composition of claim 1, wherein the particle size is less than 40 µm.

5. A calcium phosphate cement composition of claim 1, having a compressive strength of 34–39 MPa.

6. A calcium phosphate cement composition of claim 1, further comprising 15 wt % $\beta$-$Ca_3(PO_4)_2$.

7. A calcium phosphate cement composition of claim 6, wherein the composition has a compressive strength up to 50±3 MPa.

8. A method of preparing a calcium phosphate cement composition, comprising:
   a) adding a preheated $Ca(NO_3)_2 \times 4H_2O$ solution to a $(NH_4)_2HPO_4$ solution under stirring followed by addition of concentrated $NH_4OH$ solution and subsequently calcining $\beta$-calcium tertiary phosphate and hydroxyapatite to form a biphasic powder A comprising at least 95wt % $\alpha$-calcium tertiary phosphate and no more than 5 wt % hydroxyapatite;
   b) adding a $Na_2HPO_4 \times 2H_2O$ solution to a $KH_2PO_4$ solution under stirring followed by adding of $Ca(NO_3)_2 \times 4H_2O$ to form single-phase powder B $CaHPO_4 \times 2H_2O$; and
   c) mixing of powder A with powder B and subsequently milling to form the cement powder with an overall molar ratio of Ca/P of 1.35–1.40.

9. A method of claim 8, wherein powder A and powder B are mixed in a mixing ratio of 70:30 to 80:20 by weight.

10. A method of claim 8, wherein powder A and powder B are mixed in a mixing ratio of 75:25 by weight.

11. A method of claim 8, wherein the setting solution has a concentration of 3 wt %.

12. A method of claim 8, wherein the particle size of the calcium phosphate cement composition is less than 40 µm.

13. A method of claim 8, further comprising adding 15 wt % $\beta$-calcium tertiary phosphate whisker to increase the strength of the cement up to 50±3 MPa.

14. A method of claim 8, wherein a composition before calcining comprises at least 95 wt % $\beta$-calcium tertiary phosphate and no more than 5 wt % hydroxyapatite.

15. A method of claim 8, wherein the calcining is conducted at about 1200° C.

16. A method of claim 8, wherein the biphasic powder A comprises 95 wt % $\alpha$-calcium tertiary phosphate and 5 wt % hydroxyapatite.

17. A calcium phosphate cement composition, consisting essentially of:
   a biphasic powder A comprising $\alpha$-$Ca_3(PO_4)_2$ and $Ca_{10}(PO_4)_6(OH)_2$; and
   a single phase powder B comprising $CaHPO_4 \times 2H_2O$; wherein the cement has a molar ratio of Ca/P of 1.35–1.40.

18. A calcium phosphate cement composition, consisting of:
   a biphasic powder A comprising $\alpha$-$Ca_3(PO_4)_2$ and $Ca_{10}(PO_4)_6(OH)_2$; and
   a single phase powder B comprising $CaHPO_4 \times 2H_2O$; wherein the cement has a molar ratio of Ca/P of 1.35–1.40.

19. A calcium phosphate cement composition of claim 1, wherein the cement has a molar ratio of Ca/P of 1.36–1.39.

20. A method according to claim 8, further comprising mixing a mixture of powders A and B with a setting solution, $Na_2HPO_4 \times 2H_2O$.

* * * * *